United States Patent
Mason et al.

(10) Patent No.: US 11,939,421 B2
(45) Date of Patent: Mar. 26, 2024

(54) OR RELATING TO CURING AGENTS

(71) Applicant: HEXCEL COMPOSITES LIMITED, Duxford (GB)

(72) Inventors: Christopher Robert Mason, Newmarket (GB); Nicholas Verge, Letchworth (GB)

(73) Assignee: HEXCEL COMPOSITES LIMITED, Duxford (GB)

( * ) Notice: Subject to any disclaimer, the term of this patent is extended or adjusted under 35 U.S.C. 154(b) by 636 days.

(21) Appl. No.: 17/267,889

(22) PCT Filed: Aug. 30, 2019

(86) PCT No.: PCT/EP2019/073285
§ 371 (c)(1),
(2) Date: Feb. 11, 2021

(87) PCT Pub. No.: WO2020/043917
PCT Pub. Date: Mar. 5, 2020

(65) Prior Publication Data
US 2021/0198420 A1  Jul. 1, 2021

(30) Foreign Application Priority Data
Aug. 30, 2018  (GB) ..................... 1814139

(51) Int. Cl.
| C08G 59/40 | (2006.01) |
| C07C 257/22 | (2006.01) |
| C07D 235/00 | (2006.01) |
| C07D 247/02 | (2006.01) |
| C08G 59/00 | (2006.01) |
| C08G 59/68 | (2006.01) |
| C08G 59/70 | (2006.01) |
| C08K 5/25 | (2006.01) |
| C08K 5/544 | (2006.01) |

(52) U.S. Cl.
CPC .......... C08G 59/686 (2013.01); C07C 257/22 (2013.01); C07D 235/00 (2013.01); C07D 247/02 (2013.01); C08G 59/00 (2013.01); C08G 59/4014 (2013.01); C08G 59/4035 (2013.01); C08G 59/70 (2013.01); C08K 5/25 (2013.01); C08K 5/5477 (2021.01)

(58) Field of Classification Search
CPC .. C08G 59/686; C08G 59/00; C08G 59/4014; C08G 59/4035; C08G 59/70; C08G 59/40; C08G 59/68; C07C 257/22; C07D 235/00; C07D 247/02; C08K 5/25; C08K 5/5477; C08J 2363/00; C08J 5/04; C08J 5/042; C08J 5/043; C08J 5/046; C08L 63/00
USPC ......................................................... 548/100
See application file for complete search history.

(56) References Cited

U.S. PATENT DOCUMENTS

| 4,663,190 A | 5/1987 | Yuji et al. |
| 5,747,565 A | 5/1998 | Katsuji et al. |

FOREIGN PATENT DOCUMENTS

| EP | 2103600 A1 | 9/2009 |
| GB | 2323596 A | 9/1998 |
| JP | 2003-239765 A | 10/1991 |
| WO | 2016/087935 A1 | 6/2016 |

OTHER PUBLICATIONS

Search Report under Section 17(5) issued in the parent GB Application No. GB1814139.0, dated Feb. 20, 2019.
International Search Report (ISR) & Written Opinion (WO) issued in the parent Patent Cooperation Treaty (PCT), Application No. PCT/EP2019/065596, dated Sep. 26, 2019.

*Primary Examiner* — Taylor V Oh
(74) *Attorney, Agent, or Firm* — W. Mark Bielawski

(57) ABSTRACT

A curative system comprising a combination of adipic acid dihydrazide and/or isophthalic dihydrazide and a clathrate in which the guest compound of the clathrate comprises an imidazole, an imidazoline or diazabicycloalkanes (DBCA).

3 Claims, No Drawings

OR RELATING TO CURING AGENTS

The present invention relates to curative formulations and in particular to curative formulations that are useful in the curing of thermosetting resins.

BACKGROUND

Composite materials are produced in many forms. A fibrous layer impregnated with a curable resin matrix formulation is known herein as a prepreg. The resin matrix formulations in these materials may be uncured or partially cured. Moulding compounds generally comprise a fibrous material in a chopped, isotropic or quasi-isotropic form in combination with a thermosetting resin matrix formulation.

Resin matrix formulations can be selected from a wide range of polymerisable components and additives. Common polymerisable components comprise epoxies, polyesters, vinylester, polyisocyanates, and phenolics. Formulations containing these components are generally referred to as epoxy, polyester, vinylester, polyisocyanate and phenolic formulations respectively.

The properties required of a composite material are that when cured it has the required glass transition temperature (Tg), and also has the required mechanical properties for the use to which it is to be put. In certain applications it is important that the Tg is retained under damp or humid conditions ("wet Tg"). Thermosetting materials are used for structural components as they can have superior mechanical performance and creep resistance compared to thermoplastics. For these applications, the thermosetting matrix should have an initial cured Tg that is high enough to allow demoulding at the cure temperature. A higher cured Tg capability enables curing of the resin at higher cure temperature; and the use of higher cure temperature has the benefit that it will enable faster cure cycles as reactivity increases with temperature.

The cured Tg is measured in accordance with ASTM E1356 using Digital Scanning calorimetry (DSC). The retained or wet Tg is measured following isothermal curing at 150° C. for 2 minutes of the neat resin formulation and exposing the cured formulation to water at 70° C. for 14 days, and then measuring the Tg of the sample using the same measurement standard ASTM E1356.

Thermosetting resin formulations include catalysts and/or curatives, and these are selected according to the nature of the resin, the product to be produced and the cure cycle of the resin that is required. A cure cycle of composite materials to support high volume manufacturing rates, for example the manufacture of automotive components, requires very short cure cycles. Resin formulations having a cure cycle of 2.5 minutes are known and those can provide for rate manufacture of ca. 166000 parts per mould per year (assuming a second unload-re loading time and 95% utilization). It would however be desirable to shorten such a cure cycle time.

Furthermore, it is desirable to use thermosetting materials for structural components as they have superior mechanical performance and creep resistance compared to thermoplastics. The thermosetting matrix must have an initial cured Tg that is high enough to allow demoulding at the cure temperature. Accordingly, this invention seeks to provide such a resin formulation with fast cure and high Tg when cured. Materials to be utilized in the automotive industry must also be resistant to a wide variety of environmental conditions.

Very fast cure at lower temperature can be achieved with two component (2k) mixed resin systems but the equipment required to mix/meter and apply these materials makes them impractical for use in very high volume manufacturing. Additionally such methods require the construction, in an additional prior step, of a dry preform which is subsequently injected or infused with the mixed resin system; this dry preform can be time consuming to produce and difficult to position accurately into a mould particularly if it is complex shaped. Furthermore, such systems have low storage stability and it would be beneficial if fast cure high Tg resin systems could exist as a fully mixed formulation with several weeks of latency without the need for refrigeration. Such resin systems could be present in the fibrous reinforcement material at the point of their manufacture to form preimpregnated materials (prepregs) which can be cut oriented and stacked in automated processes allowing easy placement into the mould by end-users to manufacture composite parts for final curing.

Thermosetting matrix formulations which are stable (latent) at room temperature and fast curing typically use a latent amine with the cure time accelerated by a urone. Although these are effective for initial cure these curatives can lead to low in service Tg temperatures, as the latent amine and urone combination is susceptible to high levels of water uptake and matrix plasticization.

Imidazole based curatives are widely used for curing thermosetting resins. Unfortunately, these curatives are very reactive so mixtures of the resin and these curatives have the problem that they show an early on-set of curing and cannot be used as a single-component epoxy resin composition which is manufactured and then delivered at the point of use because the compositions would thicken, gel and cure in transit or in storage.

Therefore moulding materials that comprise both the fibrous reinforcement and the resin composition matrix and that can exist fully formulated and mixed with several weeks of latency or outlife without the need for refrigeration would be advantageous for composite parts manufacture.

Epoxy resin formulations are widely used in composite materials. The epoxy components in these formulations are selected from a wide range of epoxy containing materials according to the cure cycle to be employed and the nature of the finished article to be produced. Epoxy resins can be solid, liquid or semi-solid and are characterised by their functionality and epoxy equivalent weight. The functionality of an epoxy resin is the number of reactive epoxy sites per molecule that are available to react and cure to form the cured structure. For example, a bisphenol-A epoxy resin has a functionality of 2, while certain glycidyl amines can have a functionality of more than 4. The reactivity of an epoxy resin is indicated by its epoxy equivalent weight (EEW), the lower the EEW the higher the reactivity. The EEW is the weight of epoxy resin material in grams containing 1 gram/mol of epoxy groups.

Epoxy formulations also include catalysts and/or curatives, and these are also selected according to the nature of the epoxy resin, the product to be produced and the cure cycle that is required.

In matrix formulations for composite moulding materials, imidazole or imidazoline based curatives are widely used as they react readily with epoxy resins to form a cured epoxy resin matrix. Unfortunately, these curatives are very reactive so mixed solutions of epoxy resin and these curatives have the problem that they show an early on-set of curing and cannot be used as a single-component epoxy resin composition which is manufactured and then delivered at the point of use.

To overcome this problem, imidazoles have been added to hydroxybenzoic acid to form a salt. The salt has been added as a curative to epoxy resin compositions to reduce the speed of cure (see JP 4-2638).

Clathrate compositions containing a host component and a guest component that can be used as a curative composition in resin matrix compositions in moulding compounds, adhesives and prepregs are described in PCT publication WO 2016/087935 and US Patent Application publication 2010/0022744. The clathrates consist of a host compound and an imidazole or imidazoline curative as the guest component. For example, WO 2008/075427 discloses a curable resin composition using a clathrate component of an isophthalic acid-based host compound and an imidazole as guest compound. US 20120088920 discloses curable epoxy resin composition in which the curative is a clathrate based on carboxylic acids and imidazoles. US 20100179250 discloses host compounds in the form of mono carboxylic acids in which the carboxyl group is directly linked to the aromatic group and WO 2016/087935 also discloses the use of clathrates based on various carboxylic acids in combination with imidazole or imidazoline curatives.

Adipic acid dihydrazide and isophthalic acid dihydrazide are known as curatives for epoxy resin formulations. It has been suggested that they may be used together with accelerators such as urea based materials as is disclosed in U.S. Pat. Nos. 4,404,356 and 4,507,445. However there remains a need for curatives, which enable the combination of storage stability of the resin formulation prior to cure, fast cure to produce a cured resin having a high glass transition temperature (Tg) and which also retains the Tg over a period of time particularly when subjected to moisture particularly at elevated temperatures.

The invention aims to overcome the aforesaid problems and/or to provide improvements generally.

One object of the present inventions is to provide a curable epoxy resin composition having excellent storage stability, enhanced curing characteristics including faster cure and which provides a cured product having excellent mechanical properties.

According to the invention there is provided a curative system, a resin formulation, a cured resin, a use, a composite and a moulding material as defined in any one of the accompanying claims.

We have now found that if adipic acid dihydrazide and/or isophthalic dihydrazide are used together with clathrates in which the guest compound is an imidazole, an imidazoline or DBCA as a curative for thermosetting resin compositions, a fast curing resin formulation with a high glass transition temperature (Tg) combined with good Tg retention can be achieved. The use of the clathrate also imparts storage stability to the thermosetting resin composition as the host compound of the clathrate can be used to control the timing and conditions for the liberation of the imidazole or imidazoline curative.

The present invention therefore provides a curative system comprising a combination of adipic acid dihydrazide and/or isophthalic dihydrazide and a clathrate in which the guest compound comprises an imidazole, an imidazoline or diazabicycloalkanes (DBCA).

The invention further provides a resin formulation comprising a thermosetting resin and the curative system. The invention also provides the cured resin derived from such a resin.

A curative is a compound which is adapted to initiate or advance a polymerisation reaction of a polymerisable resin. The term curative includes accelerators which are chemical compounds which enhance the polymerisation reaction (or "curing") and curative agents which are chemical compounds which initiate the polymerisation reaction of a polymerisable resin.

The curative may include a curative agent, an accelerator or both of these compounds.

In a further embodiment the invention provides the use of a resin formulation of this invention as a matrix in fibre reinforced composites which may be a prepreg or may be obtained by resin infusion of dry fibrous material laid up in a mould with the resin formulation. The invention further provides a fibre reinforced composite obtained by the thermal curing of such a resin matrix.

The use of the combination of curatives in thermosetting resin systems according to this invention has produced a material which can be stored for several weeks without significant cure and can be cured in about 100 seconds by heating at 150° C. and which delivers a cured Tg in the range of from 120 to 200° C., preferably from 145 to 165° C., more preferably 155 to 165° C.

The heat released during the curing reaction is related to the total heat for fully curing and can be measured using Digital Scanning calorimetry as follows. A reference resin sample is heated from 10° C. to 250° C. at 10° C./min rate to full cure (100%) and the generated heat $\Delta Hi$ is recorded. The degree of cure of a particular resin sample of the same composition as the reference resin sample can then be measured by curing the sample to the desired temperature and at the desired rate and for the desired time by heating the sample at these conditions and measuring the heat $\Delta He$ generated by this cure reaction. The degree of cure (Cure %) is then defined by:

$$\text{Cure \%} = (\Delta He)/\Delta Hi \times 100 [\%]$$

where $\Delta Hi$ is the heat generated by the uncured resin heated from 10° C. up to fully cured at 250° C. and $\Delta He$ the heat generated by the certain degree cured resin heated up to a desired temperature and rate.

The loss modulus E' is measured in accordance with ASTM D7028 using dynamic mechanical analysis (DMA). The hot wet modulus E'w is measured using the same standard following immersion of the cured composition to water at a temperature of 70° C. for 14 days.

In the present invention, the term "clathrate" refers to a compound in which two or more molecules are bound via a bond other than a covalent bond. More preferably, it refers to a crystalline compound in which two or more molecules are bound via their molecular interaction such as via hydrogen bonds. A compound which includes one or more other compounds is referred to as the host compound and the compound or compounds included in the host compound is referred to as the guest compound. The host compound and the guest compound form the clathrate compound or structure.

The guest component of the clathrate used in this invention may operate as a curing agent or as a curing accelerator and may be quickly released from the host component by heating, and it will then undergo a crosslinking reaction with the resin component.

If the component is an accelerator, the released curing accelerator acts as a curing catalyst of the curing agent and the resin component, thereby forming a cured formulated resin matrix. The temperature at which the curing agent or the curing accelerator is released from the clathrate may be controlled according to:

the type of the guest component (chemical structure);
the type of host component (chemical structure); and
the blending ratio of the guest to the host,
solubility in the thermosetting resin
so that the release of the guest component can be controlled by selecting appropriate host and guest components to suit the thermosetting resin employed and the desired curing conditions.

In the resin formulations of the present invention, the host compound of the clathrate can react with the resin after releasing the guest compound, thereby acting as a crosslinking agent. This is particularly so when the host compound is a carboxylic acid and this can result in the cured resin formulation product having improved flexibility and improved impact resistance and adhesion.

Host Compound

In an embodiment of the invention the host component (A) may be defined by the formula (I):

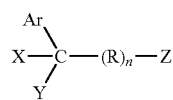

[I]

where n is 0 or 1
Ar is an optionally substituted aryl group
X is independently selected from H, OH, an optionally substituted alkyl group and an optionally substituted aryl group;
Y is independently selected from H, OH, an optionally substituted alkyl group, an optionally substituted aryl group and, taken together with Z, —C(=O)O— which forms a ring with C and R in formula I;
Z is selected from: 1) C(=O)O—R' wherein R' is selected from hydrogen, an optionally substituted hydrocarbyl group; and 2) a ring structure including Y and C
or the host component (A) is a phenolphthalein Preferably the host component (A) contains both phenolic and carboxylic acid or ester functionalities both of which are capable of forming clathrates with imidazoles. For example a preferred cost component is 4,4'-bis(4'-hydroxyphenyl) valeric acid (BHPVA) which contains both phenol and carboxylic acid functionalities. Preferably the clathrate is formed with 2-ethyl-4-methylimidazole (2E4MZ).

The host component (A) may also be phenolphtalin (PhPh) which contains bis-phenol and mono-carboxylic acid functionalities, both of which are capable of forming clathrates with imidazoles. Preferably the clathrate is formed with 2-ethyl-4-methylimidazole (2E4MZ).

In another clathrate, the host component (A) may be benzilic acid (BA) which contains phenyl and mono-carboxylic acid functionalities, which is capable of forming clathrates with imidazoles. Again, preferably the clathrate is formed with 2-ethyl-4-methylimidazole (2E4MZ).

In a further clathrate, the host component (A) may be 4-aminophenylacetic acid (APAA) containing aminophenyl and mono-carboxylic acid functionalities, both of which are capable of forming clathrates with imidazoles. Esters of these carboxylic acid based clathrates may also be selected.

Guest Compound

Instead of a single guest compound, two or more different guest compounds may be present in the clathrate. The clathrate hosts may contain different guest compounds in the same formulation such as accelerator guest compounds and/or curing agent guest compounds.

The guest compounds are imidazole compounds, imidazoline compounds or DBCA. The guest compounds may also include accelerators or a combination of curatives and accelerators.

The guest component may be selected from at least one compound selected from the group consisting of a compound represented by formula (II) and/or DBCA.

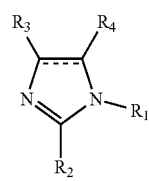

(II)

in which $R_1$ represents a hydrogen atom, a $C_1$-$C_{10}$ alkyl group, an aryl group, an arylalkyl group, or a cyanoethyl group, and $R_2$ to $R_4$ each independently represent a hydrogen atom, a nitro group, a halogen atom, a $C_1$-$C_{20}$ alkyl group, a $C_1$-$C_{20}$ alkyl group substituted with a hydroxy group, an aryl group, an arylalkyl group, or a $C_1$-$C_{20}$ acyl group; and a part with a dashed line represents a single bond or a double bond, and diazabicycloalkanes (DBCA) such as [1,8-diazabicyclo[5.4.0]undecene-7,1,4-diazabicyclo[2.2.2]octane and 1,5-diazabicyclo[4.3.0]non-5-ene.]

In an embodiment, the formula (II), $R_1$ represents a hydrogen atom, a $C_1$-$C_{10}$ alkyl group, an aryl group, an arylalkyl group, or a cyanoethyl group, but preferably represents a hydrogen atom.

The $C_1$-$C_{10}$ alkyl group is preferably a $C_1$-$C_6$ alkyl group, and optionally has a substituent. Specific examples of the $C_1$-$C_{10}$ alkyl group can include a methyl group, an ethyl group, a n-propyl group, an i-propyl group, a n-butyl group, a s-butyl group, an i-butyl group, a t-butyl group, a n-pentyl group, a n-hexyl group, a nonyl group, an i-nonyl group, and a decyl group. The aryl group means a monocyclic or polycyclic aryl group. Here, in the case of a polycyclic aryl group, the aryl group also encompasses a partially saturated group in addition to a fully unsaturated group. Examples thereof include a phenyl group, a naphthyl group, an azulenyl group, an indenyl group, an indanyl group, and a tetralinyl group. Among these groups, a $C_6$-$C_{10}$ aryl group is preferred. Further, the aryl group optionally has a substituent.

The arylalkyl group is a group in which the aryl group and the alkyl group are combined with each other. Examples thereof include a benzyl group, a phenethyl group, 3-phenyl-n-propyl group, a 1-phenyl-n-hexyl group, a naphthalen-1-ylmethyl group, a naphthalen-2-ylethyl group, a 1-naphthalen-2-yl-n-propyl group, and an inden-1-ylmethyl group. Among these groups, a $C_6$-$C_{10}$ aryl/$C_1$-$C_6$ alkyl group is preferred. Further, the arylalkyl group optionally has a substituent.

$R_2$ to $R_4$ each independently represent a hydrogen atom, a nitro group, a halogen atom, a $C_1$-$C_{20}$ alkyl group, a $C_1$-$C_{20}$ alkyl group substituted with a hydroxy group, an aryl group, an arylalkyl group, or a $C_1$-$C_{20}$ acyl group.

Examples of the $C_1$-$C_{20}$ alkyl group include a methyl group, an ethyl group, a n-propyl group, an i-propyl group, a n-butyl group, a s-butyl group, an i-butyl group, a t-butyl group, a n-pentyl group, a n-hexyl group, a nonyl group, an i-nonyl group, a decyl group, a lauryl group, a tridecyl group, a myristyl group, a pentadecyl group, a palmityl group, a heptadecyl group, and a stearyl group. A $C_1$-$C_{10}$ alkyl group is preferred.

The aryl group and the arylalkyl group include the same groups as the groups for $R_1$.

The $C_1$-$C_{20}$ acyl group means a group in which a hydrogen atom, an alkyl group, an alkenyl group, an alkynyl group, an aryl group, a heteroaryl group, or the like is combined with a carbonyl group. Examples of the acyl group include a formyl group; alkylcarbonyl groups such as an acetyl group, a propionyl group, a butyroyl group, a pentanoyl group, a hexanoyl group, a heptanoyl group, an octanoyl group, a nonanoyl group, a decanoyl group, a 3-methylnonanoyl group, an 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group, and a heneicosanoyl group; alkenylcarbonyl groups such as an acryloyl group, a methacryloyl group, an allylcarbonyl group, and a cinnamoyl group; alkynylcarbonyl groups such as an ethynylcarbonyl group and a propynylcarbonyl group; arylcarbonyl groups such as a benzoyl group, a naphthylcarbonyl group, a biphenylcarbonyl group, and an anthranilcarbonyl group; and heteroarylcarbonyl groups such as a 2-pyridylcarbonyl group and a thienylcarbonyl group. Among these groups, a 01-020 (including a carbonyl group) acyl group is preferred, and a $C_1$-$C_6$ acyl group is particularly preferred.

In a further embodiment, the guest compound may be selected from specific examples of an imidazole compound represented by formula (II) include imidazole, 2-ethyl-4-methylimidazole, 1-methylimidazole, 2-methylimidazole, 4-methylimidazole, 1-benzyl-2-methylimidazole, 2-heptadecylimidazole, 2-undecylimidazole, 2-phenyl-4-methyl-5-hydroxymethylimidazole, 2-phenylimidazole, 2-phenyl-4-methylimidazole, 1-benzyl-2-phenylimidazole, 1,2-dimethylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, and 2-phenyl-4,5-dihydroxymethylimidazole, and imidazole, 2-ethyl-4-methylimidazole, 1-methylimidazole, 2-methylimidazole, 4-methylimidazole, 1-benzyl-2-methylimidazole, 2-heptadecylimidazole, 2-undecylimidazole, 1,2-dimethylimidazole, 2-phenyl-4-methyl-5-hydroxymethylimidazole, 2-phenylimidazole, or 2-phenyl-4,5-dihydroxymethylimidazole is preferred.

Examples of the imidazoline compound represented by formula (II) include 2-methylimidazoline, 2-phenylimidazoline, 2-undecylimidazoline, 2-heptadecylimidazoline, 2-ethylimidazoline, 2-isopropylimidazoline, 2,4-dimethylimidazoline, and 2-phenyl-4-methylimidazoline, and 2-methylimidazoline or 2-phenylimidazoline is preferred.

When the imidazole compound or imidazoline compound and/or DBCA is a substance having a low boiling point or a substance having high vapour pressure, a target clathrate can be obtained by applying the vapour of these substances to the host compound.

A clathrate consisting of three components or more can also be obtained by allowing two or more types of guest compounds to react with the host compound. Furthermore, a target clathrate can be obtained by first producing a clathrate of a host compound with a certain compound and then allowing the resulting clathrate to react with a different compound in the manner as described above.

The structure of the clathrate obtained can be verified by thermal analysis (TGA-DSC, Simultaneous Thermogravimetry & Differential Scanning calorimetry), an infrared absorption spectrum (IR), an X-ray diffraction pattern, a NMR spectrum, or the like. Further, the composition of the clathrate can be verified by thermal analysis, a $^1$H-NMR spectrum, high performance liquid chromatography (HPLC), elementary analysis or the like.

Accelerator

Urea-based accelerators (or "Urones") may also be present in the curative composition. Urea-based accelerators may comprise a derivative of N, N-dimethylurea and examples of such urea-derivatives are for example N, N-diethylurea, N, N-dipropylurea, and N, N-dimethylurea. A preferred urea derivative is N, N-Dimethylurea. Specific examples are 1,1-dimethylurea or 1,1-diethylurea.

Other urones may include 1,1-dialkyl-3-aryl urea, 3-(3,4-dichlorophenyl)-1,1-dimethylurea (diuron), 3-phenyl-1,1-dimethylurea, toluyl-bis-1,1-dimethylurea, (1,1'-methylene di-p-phenylene) bis (3,3-dimethylurea), 1,1-(4-methyl-m-phenylene)bis(3,3 dimethylurea), N,N-dimethylphenylurea, 4,4-methylene diphenylene bis (N,N-dimethylurea).

The preferred urone is 4,4-methylene diphenylene bis (N, N-dimethylurea) which is present in the composition in an amount relative to the total weight of 2 to 20 wt % and more preferably 3 to 12 weight %, most preferably in an amount of the total weight of the composition with respect to 4 to 8 wt %.

In another embodiment of the invention there is provided a moulding material comprising a thermosetting resin composition of this invention in combination with a fibrous reinforcement material. The fibrous reinforcement material may be provided: as a woven fabric or a multi-axial fabric to form a prepreg, as individual fiber tows for impregnation with the resin composition to form towpregs, or as chopped fibers, short fibers or filaments to form a moulding compound. The preferred fibrous material is selected from carbon fibre, glass fibre, aramid and mixtures thereof.

In a further embodiment of the invention there is provided an adhesive comprising a thermosetting resin composition of this invention in combination with at least one filler.

The composition of this invention is storage stable and is capable of fast curing whilst the Tg, the retained Tg and mechanical properties enable use of the cured resin composition in Industrial structural applications particularly automotive and aerospace structural components as well as sporting goods and wind turbine components.

The compositions of this invention may include other typical additives used in thermosetting resins such as impact modifiers, fillers, antioxidants and the like.

Impact Modifiers

The composition may comprise an impact modifier. Impact modifiers are widely used to improve the impact strength of cured resin compositions with the aim to compensate their inherent brittleness and crack propagation. Impact modifiers may comprise rubber particles such as CTBN rubbers (carboxyl-terminated butadiene-acrylonitrile) or core shell particles which contain a rubber or other elastomeric compound encased in a polymer shell. The advantage of core shell particles over rubber particles is that they have a controlled particle size of the rubber core for effective toughening and the grafted polymer shell ensures adhesion and compatibility with the epoxy resin composition. Examples of such core shell rubbers are disclosed in EP0985692 and in WO 2014062531.

Alternative impact modifiers may include methylacrylate based polymers, polyamides, acrylics, polyacrylates, acrylate copolymers, phenoxy based polymers, and polyethersulphones.

Fillers

In addition the composition may comprise one or more fillers to enhance the flow properties of the composition. Suitable fillers may comprise talc, microballoons, flock, glass beads, silica, fumed silica, carbon black, fibers, filaments and recycled derivatives, and titanium dioxide.

Formulations

In the curing of the thermosetting resin formulations of this invention the curative is released from the clathrate by a triggered release which may be chemical, physical or a combination of both.

The chemical release may comprise a release which affects the interactions between the host component and the guest component of the clathrate by chemically altering the composition of one or both of the components.

The physical release may comprise a release which affects the interactions between the host component and the guest component of the clathrate without chemically altering the composition of the each of the components. Examples of a physical release are dissolution of the host component, an increase in temperature, a phase change of the host component, dissolution or radiation.

Clathrates based on a host compound comprising carboxylic acids and/or an esters containing an aromatic group which is linked to the carboxylic group or ester group by a divalent hydrocarbyl group and containing a curative as a guest compound are particularly suitable for curing resins particularly in one component matrix systems. Although not essential the use of such clathrates in this invention is preferred as it has been found to provide resin formulations having good control of cure conditions together with a long time until onset of curing at ambient temperature (known as outlife). The use of these clathrates also provides cured resins of high glass transition temperature (Tg) with good Tg retention. Examples of divalent optionally substituted hydrocarbyl groups useful in such clathrates include but are not limited to divalent aromatic groups or divalent aliphatic groups.

According to another aspect of the invention there is provided a curative composition containing a clathrate containing a host component and a guest component, selected from at least one compound selected from the group consisting of a compound represented by formula:

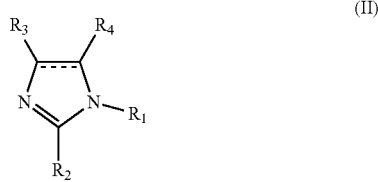

(II)

in which $R_1$ represents a hydrogen atom, a $C_1$-$C_{10}$ alkyl group, an aryl group, an arylalkyl group, or a cyanoethyl group, and $R_2$ to $R_4$ each independently represent a hydrogen atom, a nitro group, a halogen atom, a $C_1$-$C_{20}$ alkyl group, a $C_1$-$C_{20}$ alkyl group substituted with a hydroxy group, an aryl group, an arylalkyl group, or a $C_1$-$C_{20}$ acyl group; and a part with a dashed line represents a single bond or a double bond, and diazabicycloalkanes (DBCA) such as [1,8-diazabicyclo[5.4.0]undecene-7,1,4-diazabicyclo[2.2.2]octane and 1,5-diazabicyclo[4.3.0]non-5-ene.]

and adipic acid dihydrazide or isophthalic acid dihydrazide.

In the preferred clathrates the host component preferably contains a single carboxylic acid group or carboxylic acid ester group.

The mol ratio of the host component to the guest component in the clathrate is preferably in the range of from 0.5 to 2, preferably 0.7 to 1.7, more preferably from 0.9 to 1.5 and more preferably from 0.95 to 1.4 or from 0.95 to 1.1 and/or combinations of these ratios.

We have found that the use of such a clathrate together with the hydrazide as a curing agent and/or a curing accelerator for thermosetting resins, preferably epoxy resins, provides a curative having a selected onset of cure temperature which allows long term storage of one-component resin matrix systems containing highly reactive curatives.

In a further embodiment of the inventions there is provided a resin formulation comprising the curative composition of this invention in combination with at least one resin component such as an epoxy, polyisocyanate and a phenolic resin particularly an epoxy resin. The resin formulation is preferably in the form of a one-component resin formulation which does not require any further mixing of components before its use.

In another embodiment, there is provided a resin formulation comprising a curative, a resin component and a clathrate composition comprising a host component and a guest component, the guest component being a cure accelerator to enhance the curing reaction of the curative. The curative comprises adipic dihydrazide or isophthalic dihydrazide, and the guest component is an imidazole, imidazoline or DBCA based component which acts as an accelerator in combination with the hydrazide based curative. The resin is preferably an epoxy resin.

In a further embodiment there is provided a moulding material comprising a reinforcement material and the resin formulation of this invention and articles made from such moulding materials. The moulding material may be constructed from a cast resin film which contains the resin formulation and which is combined with a fibrous reinforcement layer. Preferably the resin film impregnates the fibrous reinforcement which may be accomplished by pressing a layer of resin onto the fibrous material or by infusion of the resin into fibrous material within a mould.

Where the resin is an epoxy resin it may be monofunctional or multifunctional, preferably at least difunctional. In an embodiment, the epoxy resin component (A) may be selected from various conventionally-known polyepoxy compounds. Examples thereof include: aromatic glycidyl ether compounds such as bis(4-hydroxyphenyl)propane diglycidyl ether, bis(4-hydroxy-3,5-dibromophenyl) propane diglycidyl ether, bis(4-hydroxyphenyl)ethane diglycidyl ether, bis(4-hydroxyphenyl)methane diglycidyl ether, resorcinol diglycidyl ether, phloroglucinol triglycidyl ether, trihydroxy biphenyl triglycidyl ether, tetraglycidyl benzophenone, bisresorcinol tetraglycidyl ether, tetramethyl bisphenol A diglycidyl ether, bisphenol C diglycidyl ether, bisphenol hexafluoropropane diglycidyl ether, 1,3-bis[1-(2,3-epoxypropoxy)-1-trifluoromethyl-2,2,2-trifluoroethypenzene, 1,4-bis[1-(2,3-epoxypropoxy)-1-trifluoromethyl-2,2,2-trifluoromethypenzene, 4,4'-bis(2,3-epoxypropoxy) octafluorobiphenyl, and phenolic novolac type bisepoxy compounds; alicyclic polyepoxy compounds such as alicyclic diepoxy acetal, alicyclic diepoxy adipate, alicyclic diepoxy carboxylate, and vinylcyclohexene dioxide; glycidyl ester compounds such as diglycidyl phthalate, diglycidyl tetrahydrophthalate, diglycidyl hexahydrophthalate, dimethylglycidyl phthalate, dimethylglycidyl hexahydrophthalate, diglycidyl-p-oxybenzoate, diglycidylcyclopentane-1,3-dicarboxylate, and dimer acid glycidyl ester; glycidyl amine compounds such as diglycidyl aniline, diglycidyl toluidine, triglycidyl aminophenol, tetraglycidyl diaminodiphenyl methane, and diglycidyl tribromoaniline; and heterocyclic epoxy compounds such as diglycidylhydantoin, glycidyl glycidoxyalkylhydantoin, and triglycidyl isocyanurate; and oligomer compounds thereof.

Examples of the liquid epoxy resin include polyalkylene ether type epoxy compounds such as (poly)ethylene glycol diglycidyl ether, (poly)propylene glycol diglycidyl ether, and trimethylolpropane triglycidyl ether; glycidyl ester type epoxy compounds such as dimer acid diglycidyl ester, phthalic acid diglycidyl ester, and tetrahydrophtalic acid diglycidyl ester; and homopolymers of glycidyl (meth) acrylate, allyl glycidyl ether and the like or copolymers of these monomers with other soft unsaturated monomers. In this context, soft unsaturated monomer refers to a monomer which contains a homopolymer which has a glass transition temperature of less than 60° C. Examples of soft unsaturated monomers include methyl acrylate, ethyl acrylate, butyl (meth)acrylate, isobutyl(meth)acrylate, 2-ethylhexyl(meth) acrylate, and lauryl methacrylate.

A liquid curable epoxy resin composition of the present invention is particularly useful as a one-component liquid epoxy resin prepreg matrix resin formulation which is excellent in both storage stability and curing characteristics and provides a cured product having excellent characteristics, particularly organic solvent resistance.

When the epoxy resin composition of the present invention is used as a prepreg resin formulation, known additives such as fillers, viscosity modifiers, tougheners, pigments, thixotropic agents, and fire retardants, or the like can be optionally mixed into the formulation to enhance its mechanical performance and flow behaviour during cure.

A prepreg resin formulation of the present invention can be prepared by uniformly mixing the clathrate of the invention, the resin and other additives using a pot mill, a ball mill, a bead mill, a roll mill, a homogenizer, Supermill, Homodisper, a universal mixer, Banbury mixer, a kneader, or the like.

Since the prepreg resin formulation of the present invention can be a one-component type that has both high storage stability and excellent thermosetting properties, it can be suitably used for applications which require long term storage or storage in unconditioned facilities at room temperature.

The invention is illustrated by reference to the following examples in which the following materials were used.

Adipic Acid Dihydrazide (ADH/ADH-J)
4,4'-Methylene diphenylene bis(N,N-dimethyl urea) (urone accelerator)
Epoxy Phenol Novolac Resin (Novolac)
Bisphenol A diglycidyl ether resin (BADGE)
Bisphenol A (BPA)
4,4'-Bis(4'-hydroxyphenyl)valeric acid-2E4MZ clathrate (BHPVA-2E4MZ)
Phenolphthalin-IMZ clathrate (PhPh-IMZ)
4,4-Bis(p-hydroxyphenyl)propionic acid-2E4MZ clathrate (BHPPA-2E4MZ)
2-Ethyl-4-methylimidazole (2E4MZ)

The following parameters were measured in accordance with the following standards and protocols.

Parameter (unit) Description

Tg (° C.) Tg is measured using Differential Scanning calorimetry (DSC) in accordance with ASTM E1356, "Standard Test Method for Assignment of the Glass Transition Temperature by Differential Scanning calorimetry" for an isothermally cured composition at 150° C.

Outlife @ 23° C. (weeks) resin composition is stored at 23° C. and is sampled on half weekly intervals to measure the Tg in accordance with ISO 11357-1:2016 using Digital Scanning calorimetry (DSC). Outlife is confirmed for the weekly measurement when the measured Tg of the uncured resin is equal to or exceeds the storage temperature of 23° C.

Time to cure at 150° C. A Mettler Toledo Differential Scanning Calorimeter (DSC), model DSC-1 was used to measure the total reaction enthalpy for a composition in relation to time and to establish the time taken to reach 95% cure. To establish the total reaction enthalpy of the resin composition during isothermal cure at 150° C., the composition was held at this temperature for 30 mins to ensure full cure which was evidenced by showing no changes in cumulative heat enthalpy output. Once the total heat enthalpy had been established, the time to 95% cure could be readily derived from the cumulative heat enthalpy in relation to time.

EXAMPLES 1 TO 7

The following formulations with varying curative systems were prepared, each containing varying amounts of an imidazole in combination with ADH. All amounts for the components are in weight % (wt %) in relation to the total weight of the composition.

| | Example | | | | | | |
|---|---|---|---|---|---|---|---|
| | 1 | 2 | 3 | 4 | 5 | 6 | 7 |
| Curative system | ADH/ Urone 2E4MZ | ADH/ Urone 2E4MZ | ADH BHPVA- 2E4MZ | ADH PhPh- IMZ | ADH BHPPA- 2E4AMZ | ADH PhPh- IMZ | ADH PhPh- IMZ |
| Novolac (wt %) | 45 | 45 | 37 | 29 | 37 | 24 | 36 |
| BPA-Type 1 (wt %) | 20 | 20 | 16 | 16 | 16 | 16 | 16 |
| BADGE (wt %) | 18.5 | 18 | 29 | 29 | 29 | 29 | 29 |
| ADH (wt %) | 9 | 9 | 7 | 7 | 7 | 7 | 7 |
| Urone (wt %) | 7 | 7 | | | | | |

|  | Example | | | | | | |
|---|---|---|---|---|---|---|---|
|  | 1 | 2 | 3 | 4 | 5 | 6 | 7 |
| Curative system | ADH/ Urone 2E4MZ | ADH/ Urone 2E4MZ | ADH BHPVA-2E4MZ | ADH PhPh-IMZ | ADH BHPPA-2E4AMZ | ADH PhPh-IMZ | ADH PhPh-IMZ |
| BHPVA-2E4MZ (wt %) |  |  | 11 |  |  |  |  |
| PhPh-IMZ (wt %) |  |  |  | 19 |  | 24 | 12 |
| BHPPA-2E4MZ (wt %) |  |  |  |  | 11 |  |  |
| 2E4MZ (wt %) | 0.5 | 1 |  |  |  |  |  |
| Outlife @ 23° C. (weeks) | 1.5 | 3 | 6 | 6 | 6 | 6 | 6 |
| Time to 95% cure at 150° C. (min) | 2.7 | 3.2 | 1.7 | 1.1 | 1.6 | 1 | 1.6 |
| Tg (° C.) | 145 | 144 | 156 | 155 | 158 | 124 | 163 |
| Active amount of Imidazole (wt%) | 0.5 | 1 | 3 | 3 | 3 | 4 | 2 |

The materials were stored at 23° C. and the time to onset of cure determined. The clathrate and adipic acid dihydrazide containing formulations were compared with formulations containing adipic acid, dihydrazide and a free imidazole. In every instance the time to onset of cure for the clathrate containing formulations (Examples 3 to 7) was about double the time for the free imidazole containing formulations (Examples 1 and 2).

The resin formulations were exposed to a temperature of 150° C. to isothermally cure the compositions and the time to peak exotherm and the time to reach 95% cure were measured. The time from the onset of cure to 95% cure when heated to 150° C. for the clathrate containing formulations (Examples 3 to 7) was less than half the time required for the free imidazoline containing formulations (Examples 1 and 2) whereas the Tg was in most instances at least 30% higher with the clathrate containing formulations.

EXAMPLES 8 TO 11

Basic formulations were prepared with a difunctional epoxy resin component and varying curative systems. The active amount of imidazole was varied in the different curative systems which each contain ADH. These formulations were again cured isothermally at 150° C.

|  | Example | | | |
|---|---|---|---|---|
|  | 8 | 9 | 10 | 11 |
|  | Curative system | | | |
|  | Urone/ADH | ADH/ imidazole (1% imidazole content) | ADH/ clathrate (3% imidazole content) | Urone/ clathrate (3% imidazole content) |
| Time to 95% cure at 150° C. (min) | 4.6 | 2.6 | 1.8 | 5 |
| Tg (° C.) | 135 | 145 | 157 | 148 |
| Active amount of Imidazole |  | 1.00 | 3.00 | 3.00 |

The effect of a curative system was compared in relation to the time to cure at 150° C. and Tg for formulations of the same resin component in relation to curative systems containing (i) Urone plus adipic acid dihydrazide (ii) Adipic acid dihydrazide plus Imidazole (iii) Adipic acid dihydrazide plus clathrate (iv) Urone plus clathrate.

The formulation containing the adipic acid dihydrazide clathrate combination had the shortest time to reach 95% cure when heated to 150° C. and also had the highest cured Tg of 157° C.

The invention claimed is:

1. A curative composition comprising a combination of adipic acid dihydrazide or isophthalic dihydrazide and a clathrate, said clathrate comprises a host component and a guest component, said guest component comprising at least one compound selected from the group consisting of a compound represented by formula:

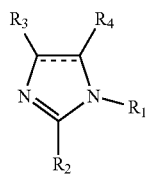

in which $R_1$ represents a hydrogen atom, a $C_1$-$C_{10}$ alkyl group, an aryl group, an arylalkyl group, or a cyanoethyl group, and $R_2$ to $R_4$ each independently represent a hydrogen atom, a nitro group, a halogen atom, a $C_1$-$C_{20}$ alkyl group, a $C_1$-$C_{20}$ alkyl group substituted with a hydroxy group, an aryl group, an arylalkyl group, or a $C_1$-$C_{20}$ acyl group; and a part with a dashed line represents a single bond or a double bond, and diazabicycloalkanes (DBCA); and said host component comprising 4,4'-bis(4'-hydroxyphenyl) valeric acid (BHPVA) or 4,4-bis(p-hydroxyphenyl) propionic acid (BHPPA).

2. The curative composition according to claim 1, further comprising a urea-based accelerator.

3. A moulding material comprising a thermosetting resin composition according to claim 2 in combination with a fibrous reinforcement material.

* * * * *